US008830572B2

(12) United States Patent
Graber

(10) Patent No.: US 8,830,572 B2
(45) Date of Patent: Sep. 9, 2014

(54) STAND FOR A MICROSCOPE, IN PARTICULAR A SURGICAL MICROSCOPE

(75) Inventor: Michael Graber, Horn (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 608 days.

(21) Appl. No.: 13/039,425

(22) Filed: Mar. 3, 2011

(65) Prior Publication Data

US 2011/0216402 A1    Sep. 8, 2011

(30) Foreign Application Priority Data

Mar. 4, 2010    (DE) .......................... 10 2010 010 131

(51) Int. Cl.
G02B 21/00 (2006.01)
F16M 11/10 (2006.01)
G02B 7/00 (2006.01)
G02B 21/24 (2006.01)
A61B 19/00 (2006.01)

(52) U.S. Cl.
CPC .............. G02B 21/24 (2013.01); G02B 7/001 (2013.01); A61B 2019/263 (2013.01); A61B 19/26 (2013.01); G02B 21/0012 (2013.01); A61B 19/5223 (2013.01); F16M 11/10 (2013.01)
USPC .. 359/384; 359/368; 248/123.11; 248/281.11

(58) Field of Classification Search
CPC .......... G02B 7/00; G02B 7/001; G02B 21/00; G02B 21/0012; A61B 19/26; A61B 19/5223; F16M 11/10; F16M 11/12; F16M 11/24; A47F 5/00; A47F 5/10
USPC ........................................ 359/368, 382, 384
See application file for complete search history.

(56) References Cited

U.S. PATENT DOCUMENTS

| 5,345,334 | A | * | 9/1994 | Heller ........................... 359/393 |
| 5,651,718 | A | * | 7/1997 | Nakamura ................. 248/123.2 |
| 5,818,638 | A | * | 10/1998 | Nakamura .................... 359/384 |
| 6,045,104 | A | | 4/2000 | Nakamura et al. |
| 6,105,909 | A | * | 8/2000 | Wirth et al. ................ 248/123.2 |
| 6,199,812 | B1 | | 3/2001 | Schuepbach |
| 6,254,046 | B1 | | 7/2001 | Biber |
| 6,592,086 | B1 | | 7/2003 | Sander |
| 8,205,845 | B2 | * | 6/2012 | Hammer .................... 248/276.1 |
| 8,520,302 | B2 | * | 8/2013 | Graber .......................... 359/384 |
| 2005/0247831 | A1 | | 11/2005 | Nakamura |
| 2009/0218455 | A1 | | 9/2009 | Metelski |
| 2009/0219613 | A1 | | 9/2009 | Enge |

* cited by examiner

Primary Examiner — Thong Nguyen
(74) Attorney, Agent, or Firm — Hodgson Russ LLP

(57) ABSTRACT

A microscope stand (11) is disclosed, including at least one pivot support (12), a mount (22) attached to a first end (15) of the pivot support (12), and a C-slide displacement assembly (112). The pivot support (12) is held to a stand interface (14) by a parallel guide mechanism (116), which allows the pivot support (12) to perform a circular motion in a vertical plane. The parallel guide mechanism (116) is formed by a cross-lever linkage which is rotatable about a cross-lever axis (115) extending centrally between and parallel to the support axis (113) of the pivot support (12) and the pivot axis (114) of the C-slide displacement assembly (112) and which is connected to both the stand interface (14) and the pivot support (12) in such a way that it transmits its own pivotal state simultaneously and equally to the stand interface (14) and to the pivot support (12).

14 Claims, 20 Drawing Sheets

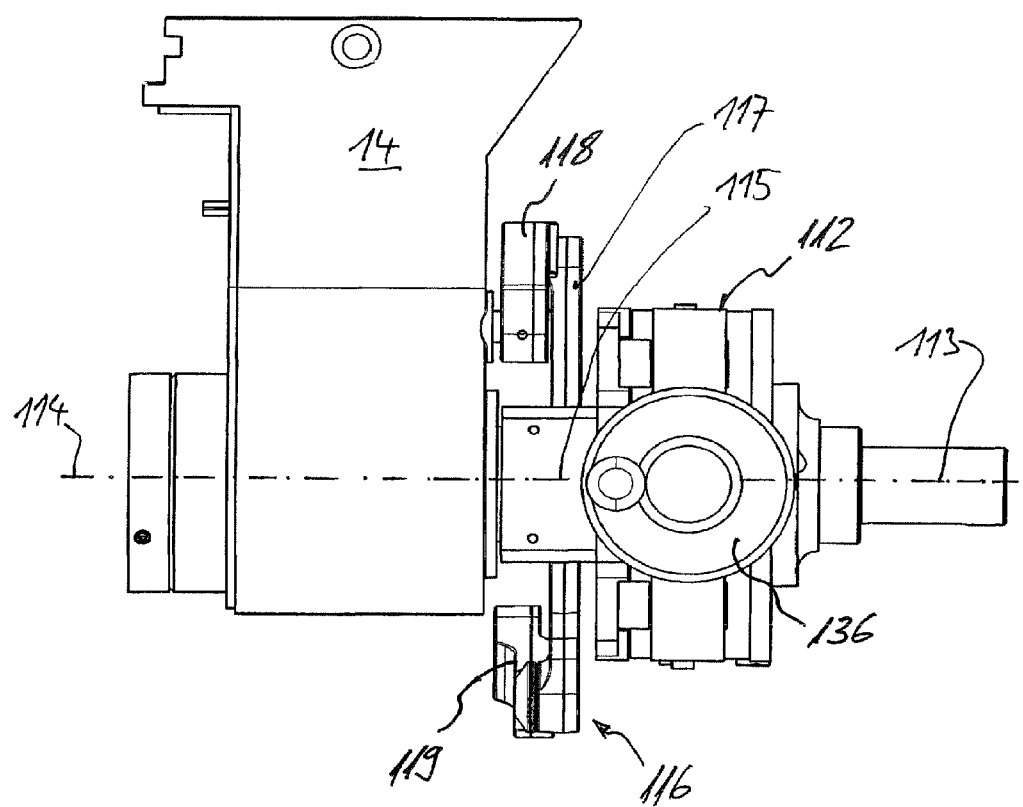

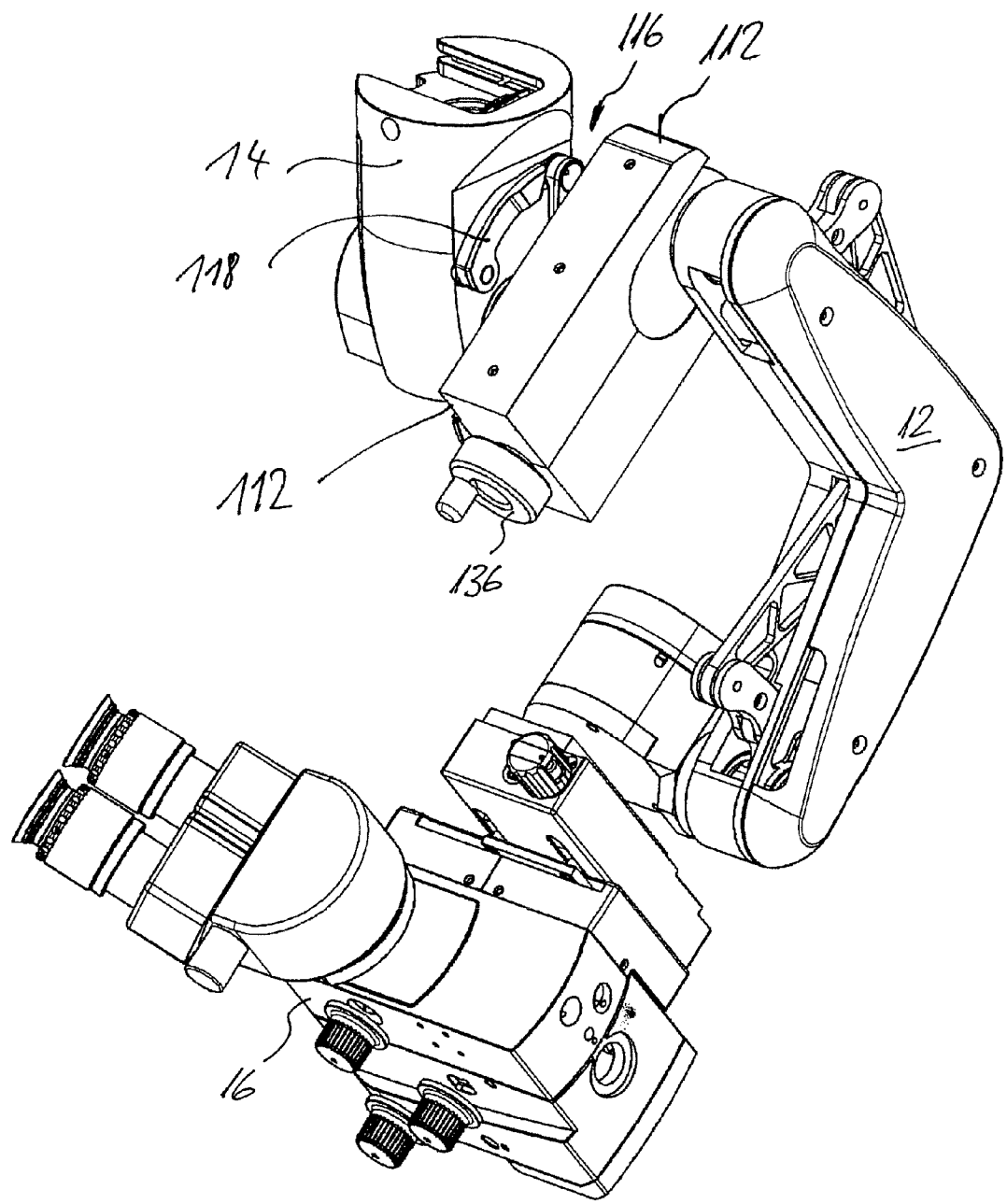

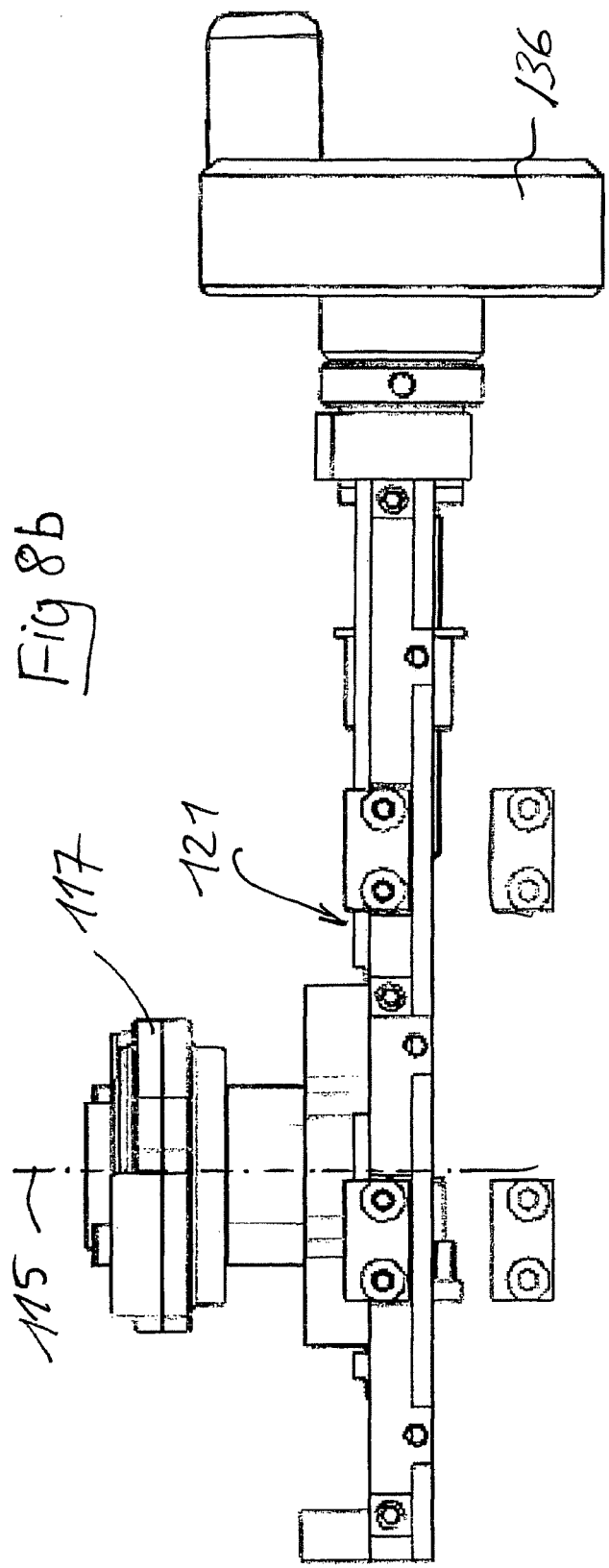

STAND FOR A MICROSCOPE, IN PARTICULAR A SURGICAL MICROSCOPE

CROSS REFERENCE TO RELATED APPLICATIONS

This application claims priority of German patent application number 10 2010 010 131.1 filed Mar. 4, 2010, the entire disclosure of which is incorporated by reference herein.

FIELD OF THE INVENTION

The present invention relates to a microscope stand, in particular to a stand for a surgical microscope, of the type comprising at least one pivot support, a mount attached to a first end of the pivot support and adapted to mount the microscope to the microscope stand, and further comprising a C-slide displacement assembly provided on the second end of the pivot support for balancing the microscope about a pivot axis associated with a stand interface; the pivot support being pivotable about a support axis/axle held by the C-slide displacement assembly; the C-slide displacement assembly being pivotable about the pivot axis relative to the stand interface; the pivot support being held to the stand interface by a parallel guide mechanism, which allows the pivot support to perform a circular motion in a vertical plane.

BACKGROUND OF THE INVENTION

Microscopes, particularly surgical microscopes, are supported by microscope stands and surgical microscope stands, respectively, which are either placed on a floor or a piece of furniture or equipment, or mounted to a wall or ceiling.

Commonly owned international patent application WO-A1-98/52484 describes a microscope stand, in particular, a stand for a surgical microscope, including a pivot support, a mount attached to a first end of the pivot support and adapted to mount the microscope to the microscope stand, and a C-slide displacement assembly provided on the second end of the pivot support for balancing the microscope about a pivot axis associated with a stand interface. The pivot support is pivotable about an axis defined by a support axle held by the C-slide displacement assembly. The C-slide displacement assembly is pivotable about a pivot axis relative to the stand interface. All pivoting movements can be suppressed, typically by braking force, so as to prevent the elements of the microscope stand from being unintentionally moved out of adjustment. The pivot support is held to the stand interface by a parallel guide mechanism having linear guides, which allows the pivot support to perform a tilt-free circular motion in a vertical plane. This microscope stand enables the microscope to be guided vertically during pivoting of the pivot support, and enables balancing of different weight configurations on the microscope with respect to the pivot axis, which typically intersects a vertical axis of rotation in the stand.

However, the drawback of the known approach is that, as the pivot support is pivoted, the linear guides of the parallel guide mechanism may make noises which may be perceived as annoying by some users and, in addition, the parallel guide mechanism has a relatively high weight. Furthermore, such a known parallel guide mechanism requires a large amount of space, especially because it must include parallel guides for both the horizontal and vertical directions.

Therefore, there is still a need to improve a microscope stand, and in particular a stand for a surgical microscope, in such a way that it does not have the aforementioned disadvantages and, in particular, that it is compact and easy to manufacture, and makes less noise during adjustment.

SUMMARY OF THE INVENTION

This object is achieved by the features of the independent claims. Advantageous embodiments are illustrated in the figures and described in the dependent claims.

In accordance with the present invention, the parallel guide mechanism is formed by a cross-lever linkage which is rotatable about a cross-lever axis extending centrally between and parallel to the pivot support axis and the pivot axis of the C-slide displacement assembly and which is connected to both the stand interface and the pivot support in such a way that it transmits its own pivotal state simultaneously and equally to the stand interface and to the pivot support and prevents tilting of the pivot support during changes in the spatial position thereof.

Thus, similar to the two known parallel guides, the cross-lever linkage ensures vertical orientation of the microscope during pivoting of the pivot support. Because of the cross-lever linkage, this portion of the microscope stand has a much smaller space requirement and less weight than a parallel guide mechanism having linear guides. Therefore, the parallel guide mechanism, and thus the microscope stand, can be made more compact and lighter. In addition, due to its pivotable parts, the cross-lever linkage makes no or only little noise as compared to linearly guided parts.

Just as the information provided in the patent claims, the list of reference numerals is part of the disclosure.

BRIEF DESCRIPTION OF THE DRAWING VIEWS

The present invention is schematically described in more detail by way of example and with reference to figures.

The figures are described collectively. Identical reference numerals denote identical components; reference numerals having different indices indicate functionally identical or similar components.

In the drawing,

FIG. 3a is a detail view of the C-slide displacement assembly according to line IV-IV in FIG. 2;

FIG. 5 is a perspective rear view of the microscope stand, showing the C-slide displacement assembly in a second position different from the first position (cf. FIG. 4);

FIG. 6 is a view showing the microscope stand from a side opposite to that shown in the detail view of FIG. 3a;

FIG. 8b is a side view of the central slide plate of the C-slide displacement assembly;

DETAILED DESCRIPTION OF THE INVENTION

Figure 1:
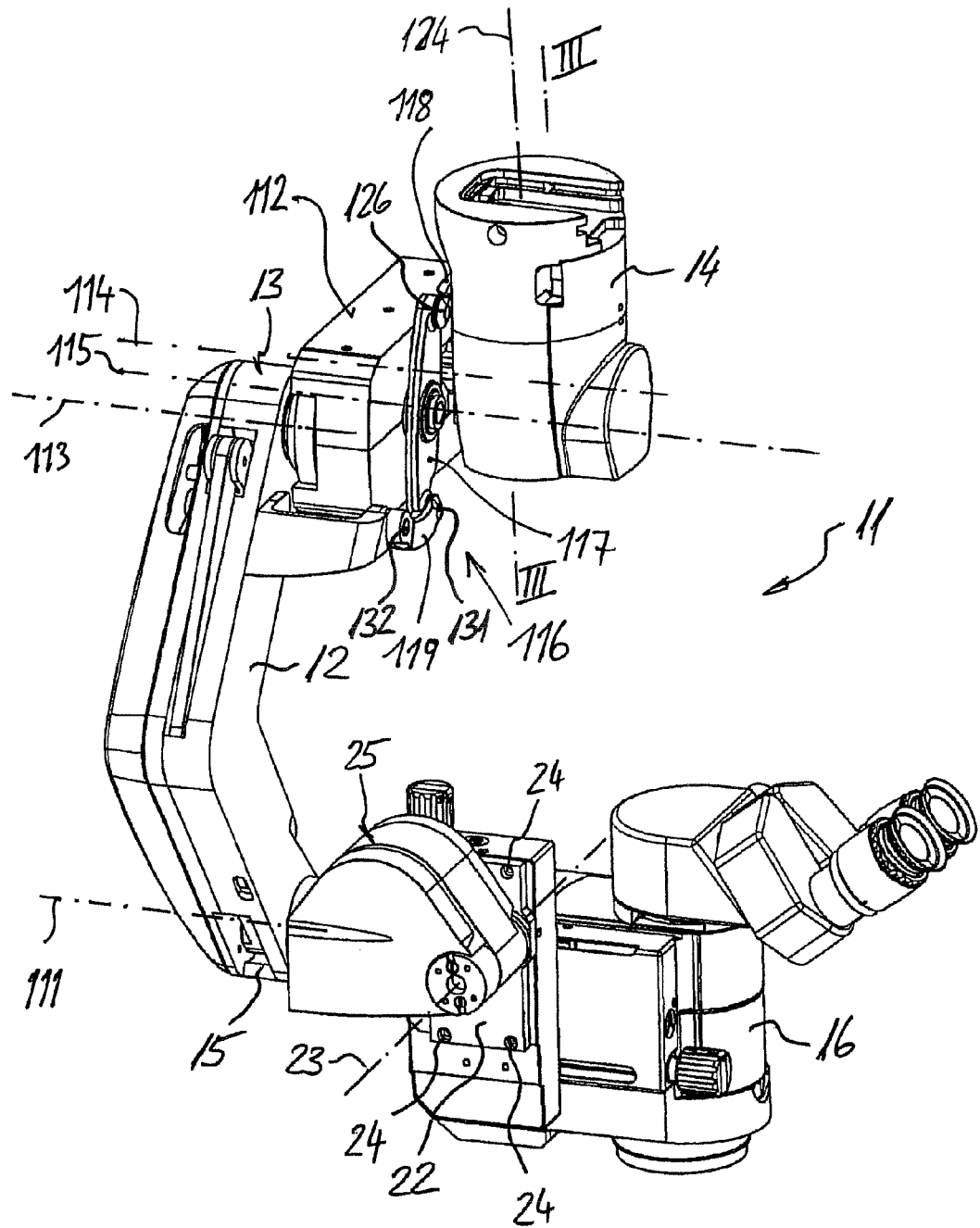
FIG. 1 is a perspective front view of a microscope stand, showing the C-slide displacement assembly in a first position.
Figure 2:
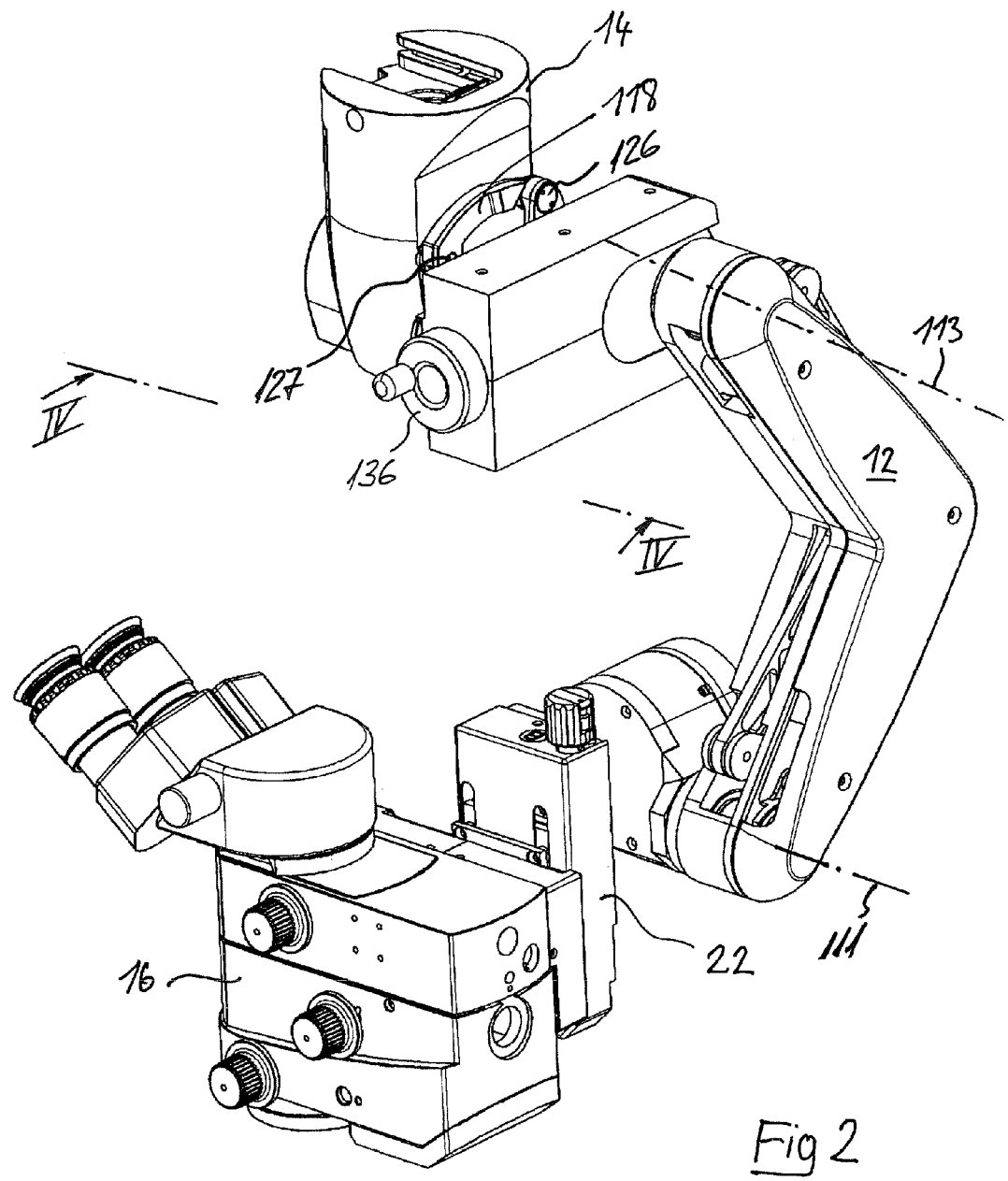
FIG. 2 is a perspective rear view of the microscope stand of FIG. 1.
Figure 3:
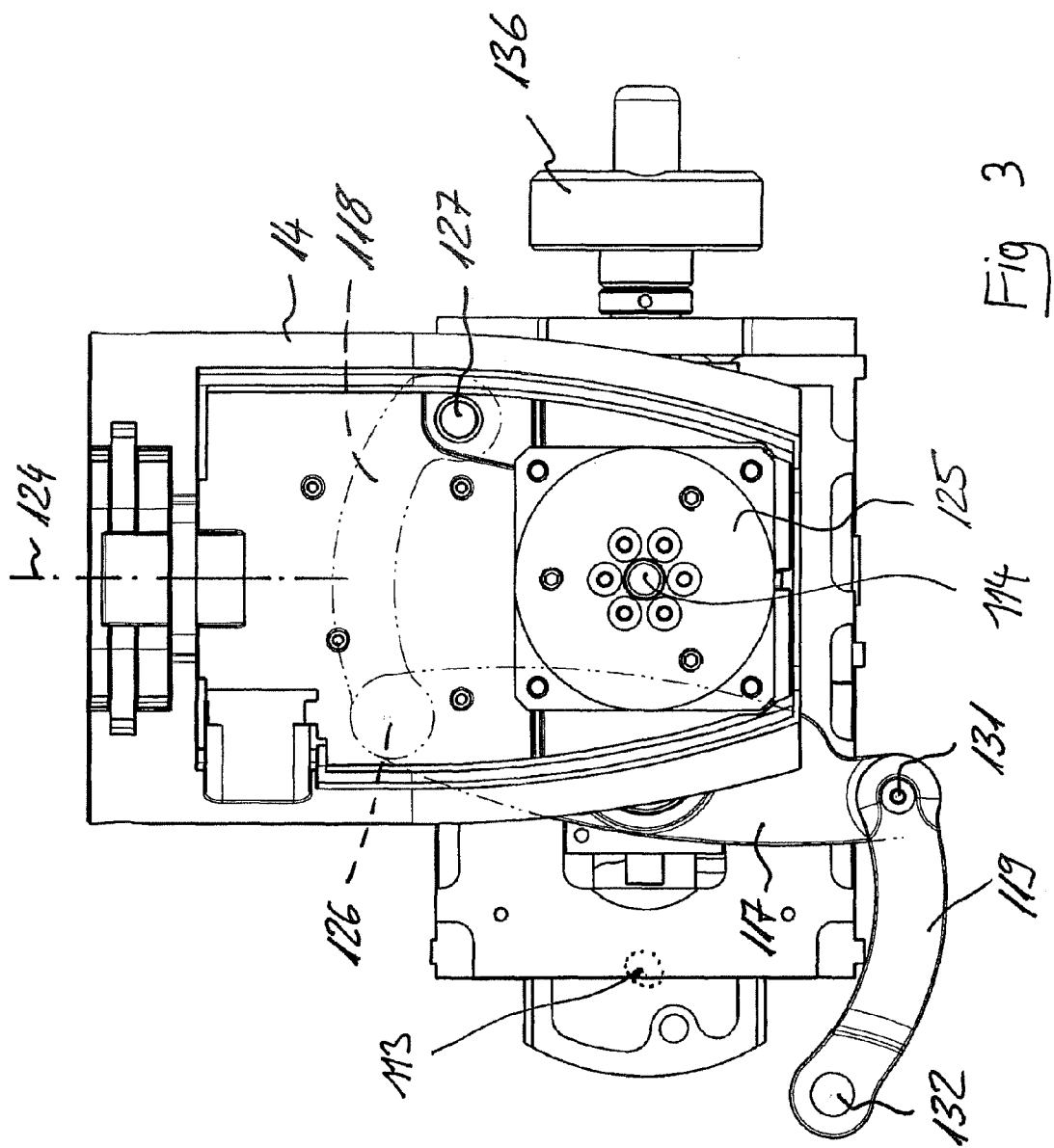
FIG. 3 is a partial section through the stand interface, taken along line III-III in FIG. 1 and showing the C-slide displacement assembly in the first position.
Figure 4:
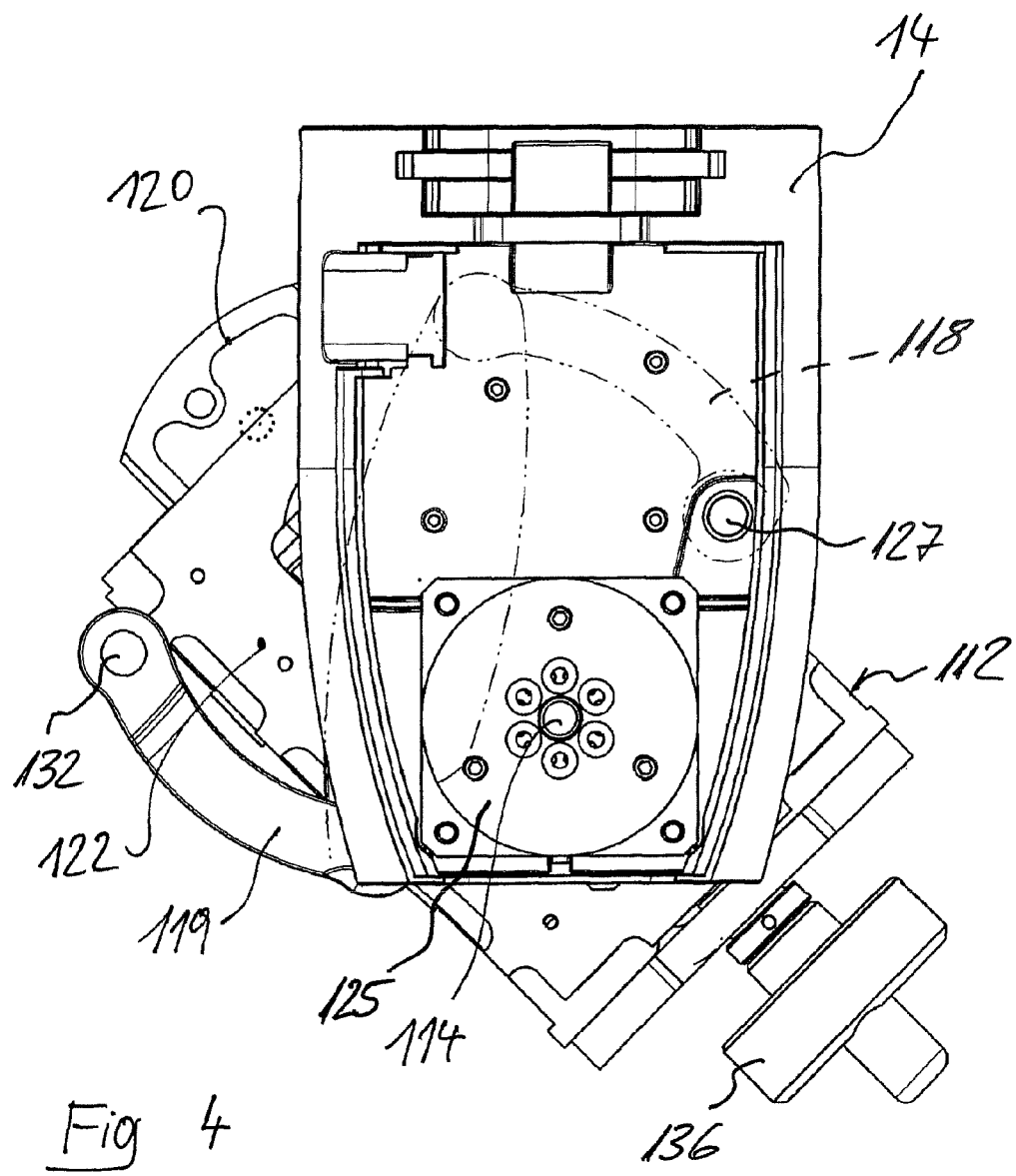
FIG. 4 is a partial section similar to FIG. 3, showing the stand interface with the C-slide displacement assembly in a second position different from the first position shown in FIG. 1.
Figure 5A:
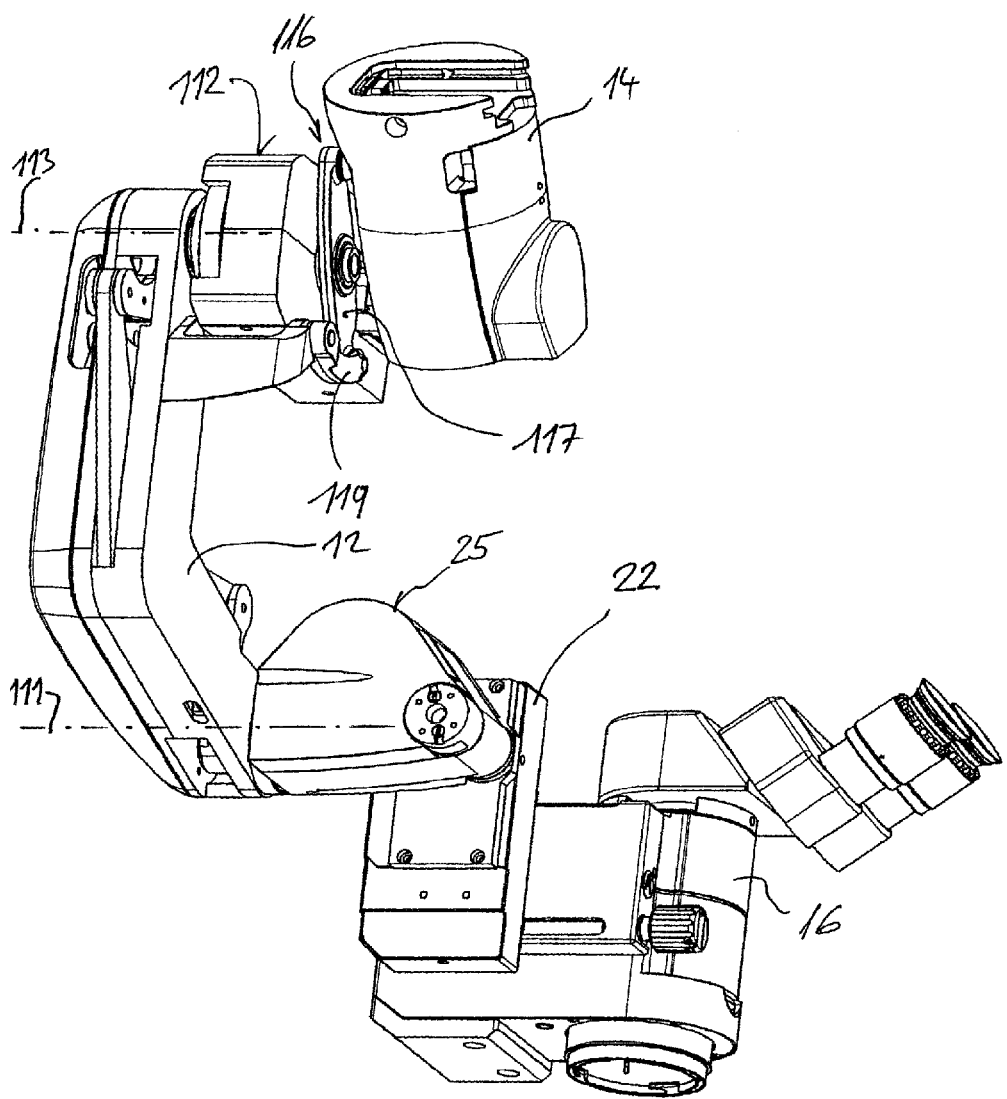
FIG. 5a is a perspective side view showing the microscope stand of FIG. 5 in the second position.
Figure 6:
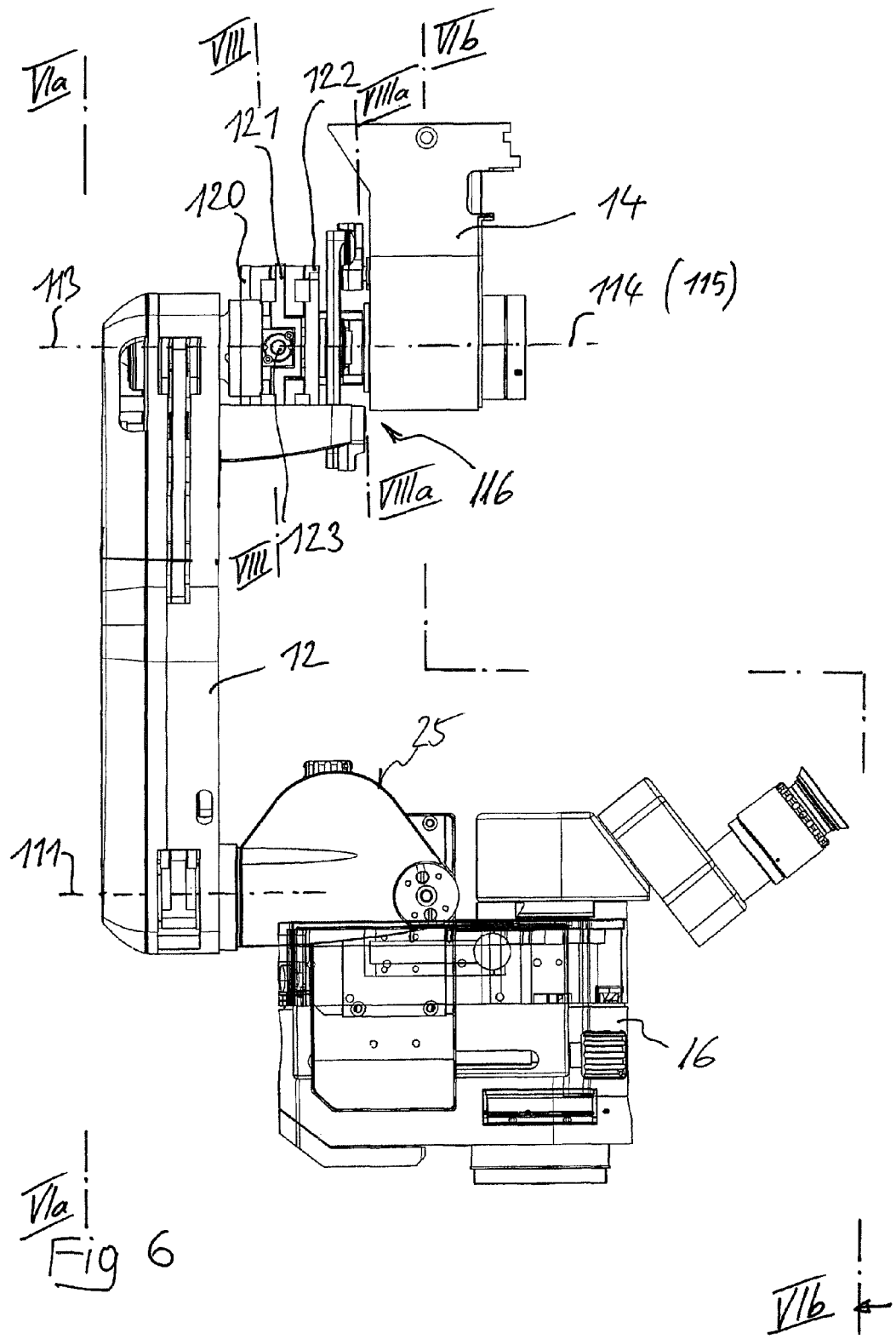
Figure 6A:
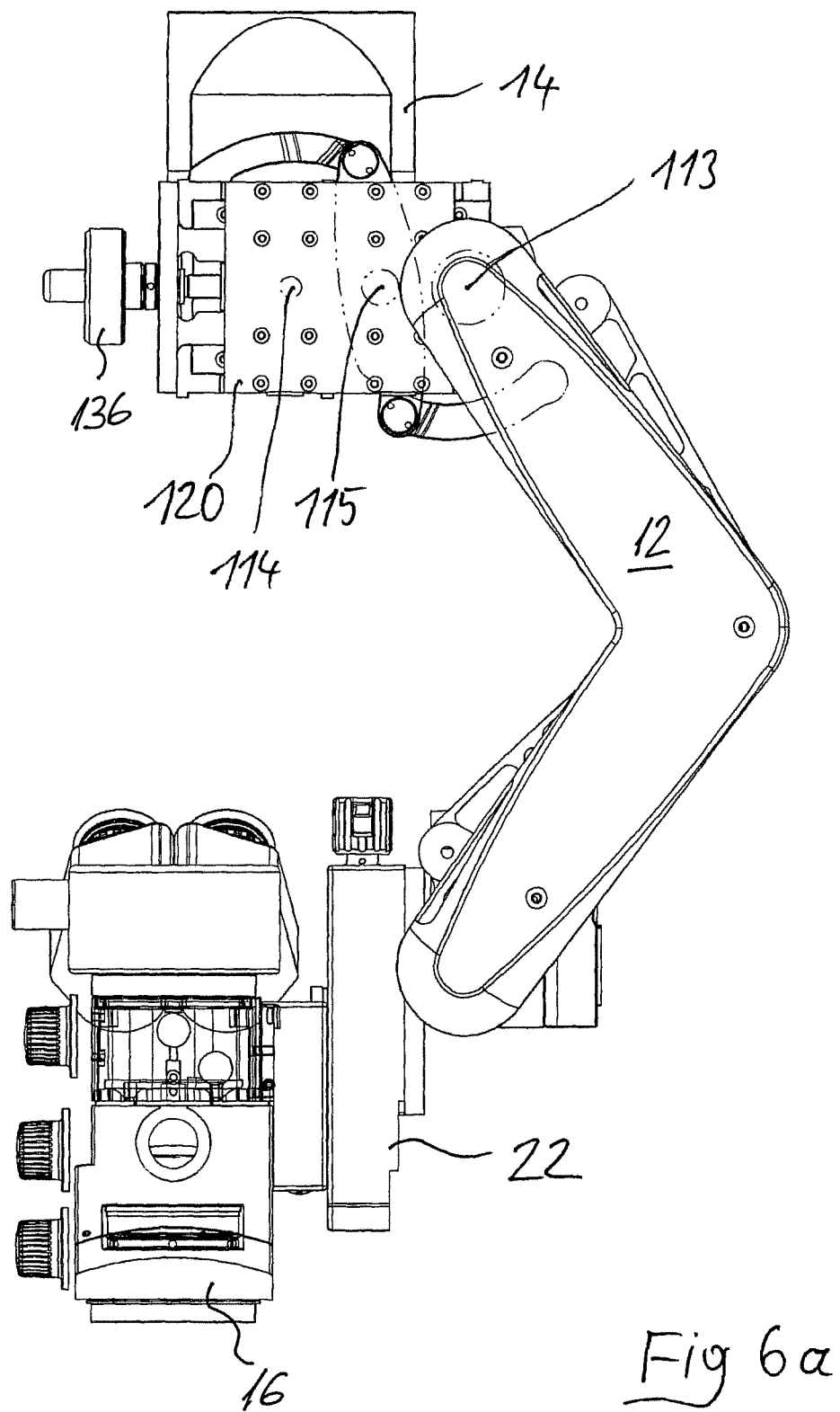
FIG. 6a is a view of the microscope stand taken along line VIa-VIa in FIG. 6.
Figure 6B:
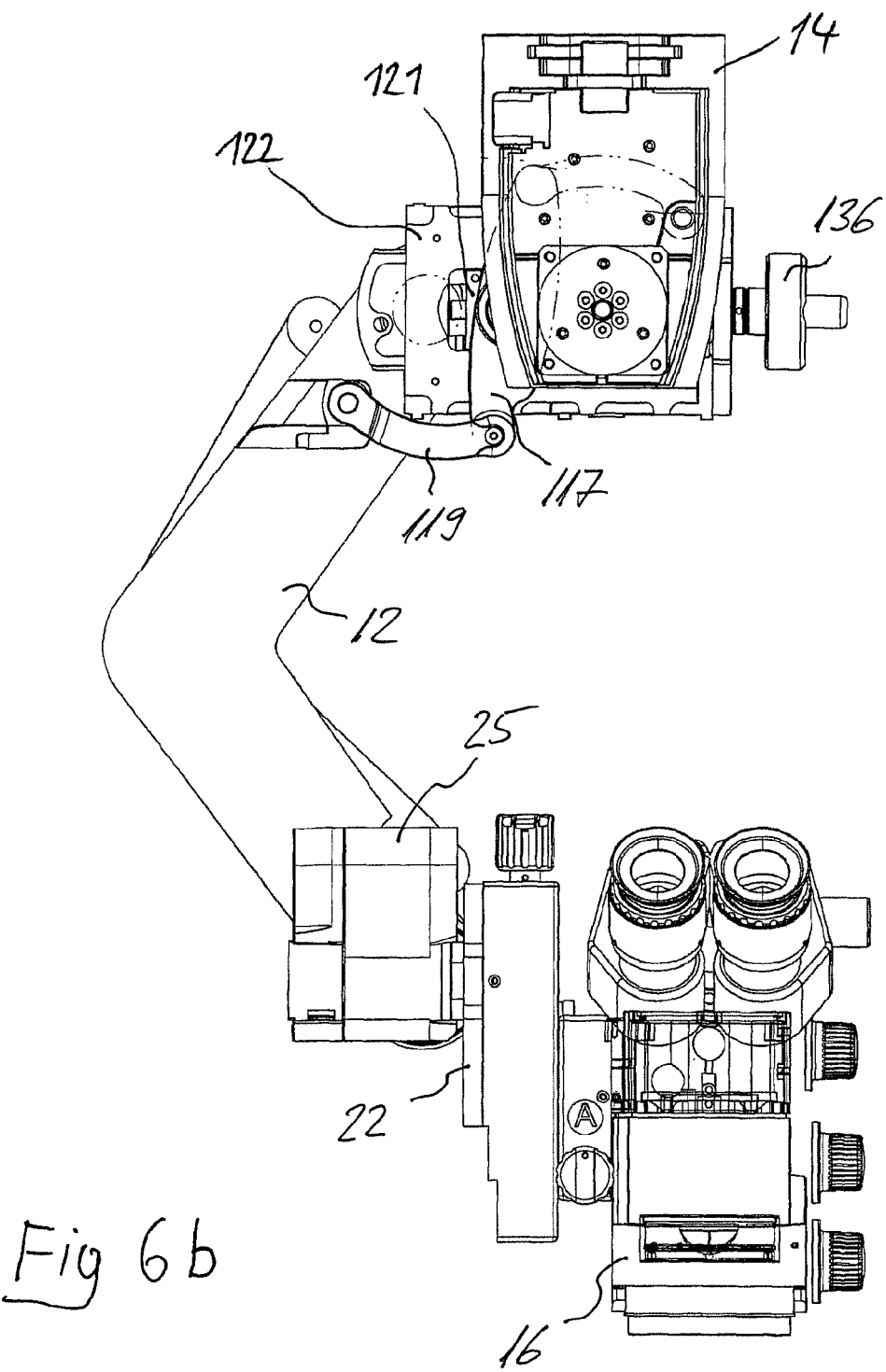
FIG. 6b is a view of the microscope stand taken along line VIb-VIb in FIG. 6.
Figure 7:
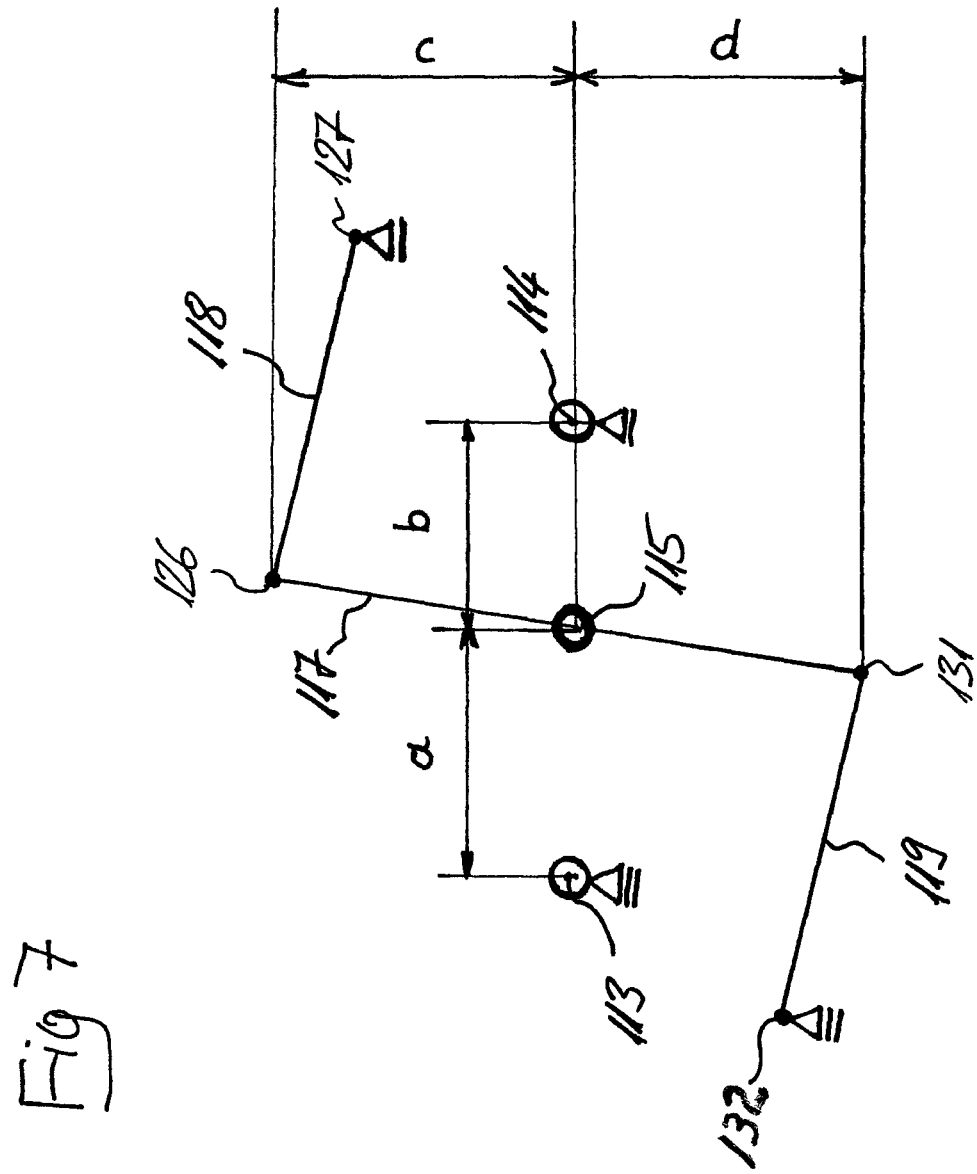
FIG. 7 is a schematic diagram of the lever arrangement and pivot points of the cross-lever linkage.
Figure 8:
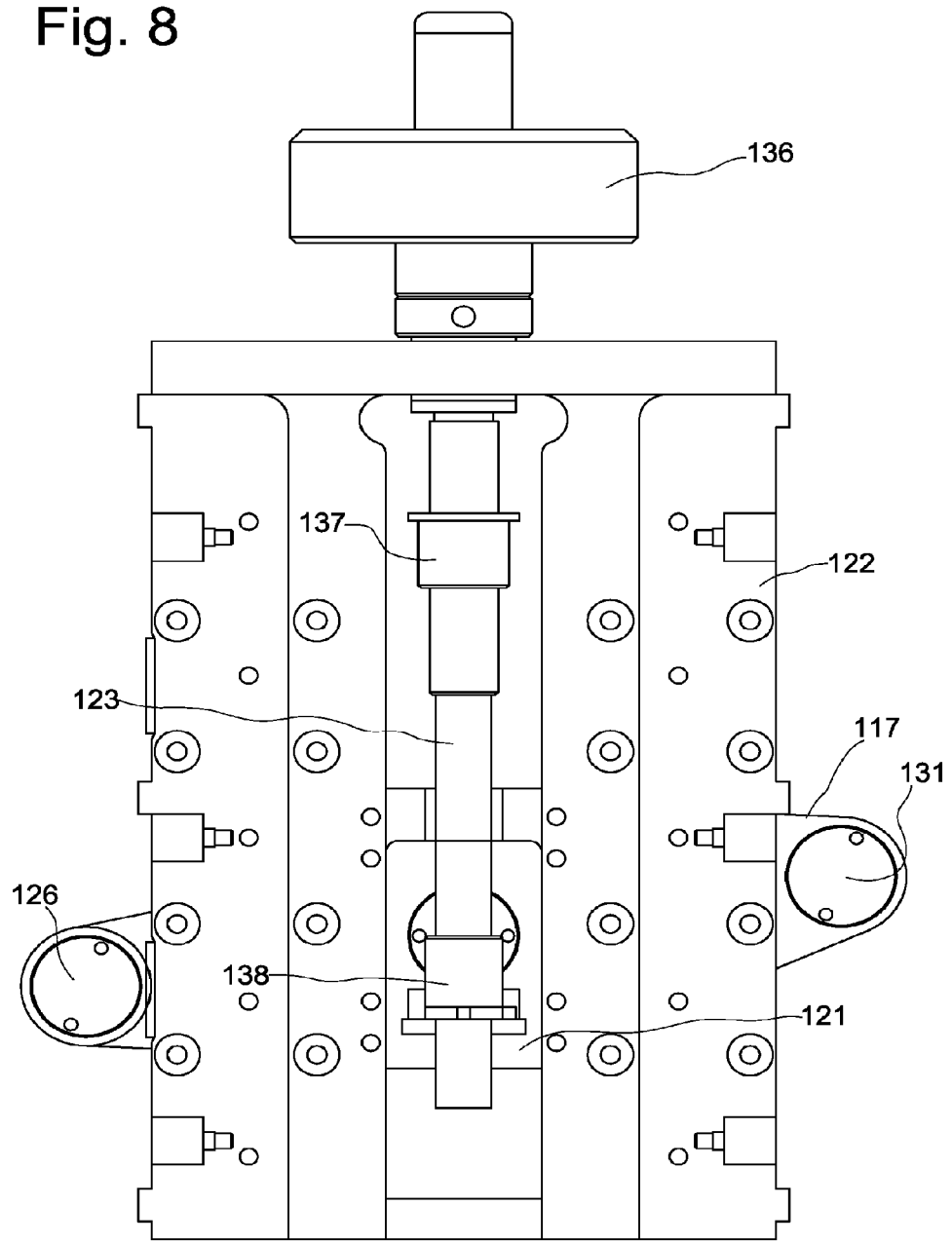
FIG. 8 is a view of the C-slide displacement assembly taken along line VIII-VIII in FIG. 6.
Figure 8A:
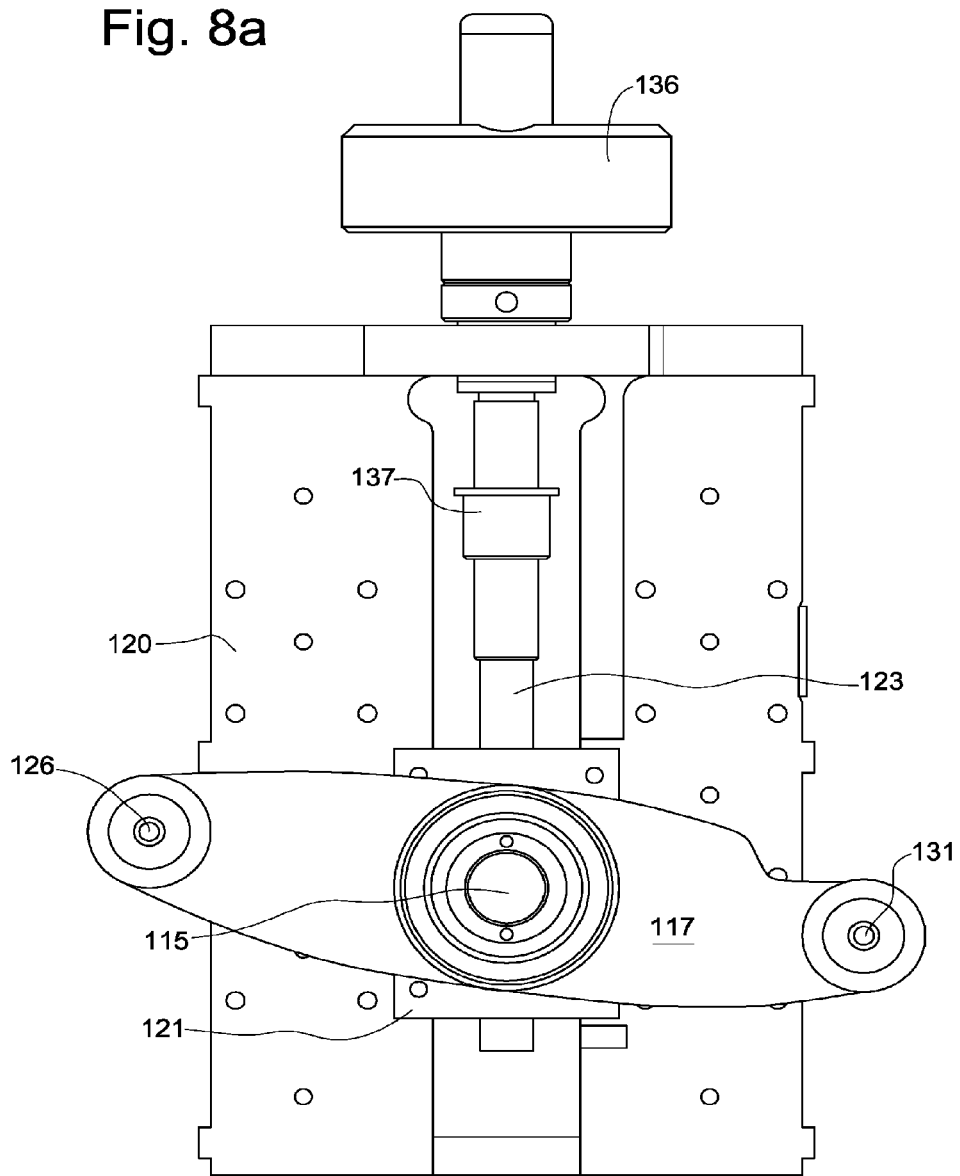
FIG. 8a is a view of the C-slide displacement assembly taken along line VIIIa-VIIIa in FIG. 6.
Figure 9:
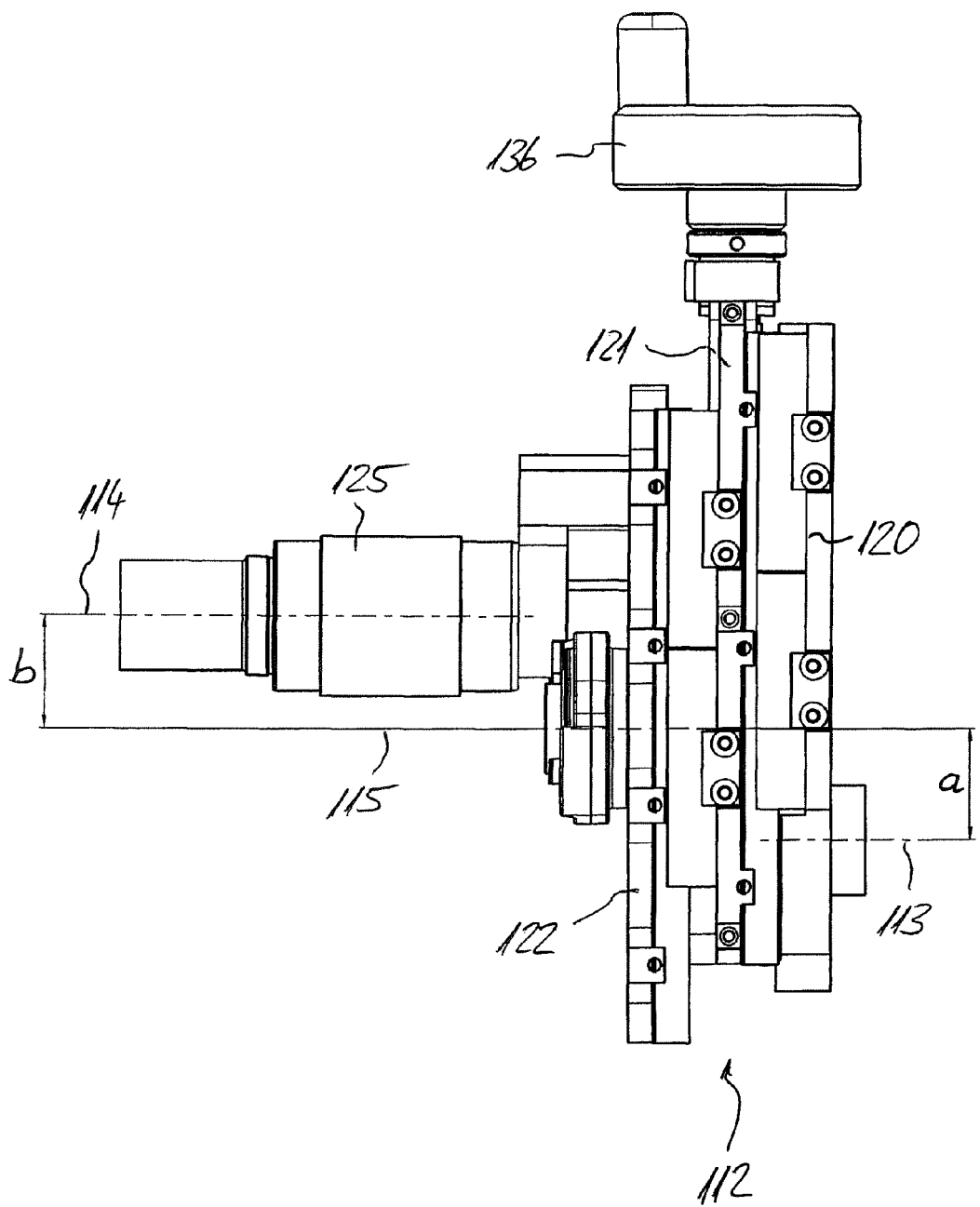
FIG. 9 is a plan view showing the C-slide displacement assembly and the pivot axes in a first balanced condition in which there is a small distance between the pivot support axis and the cross-lever axis.
Figure 10:
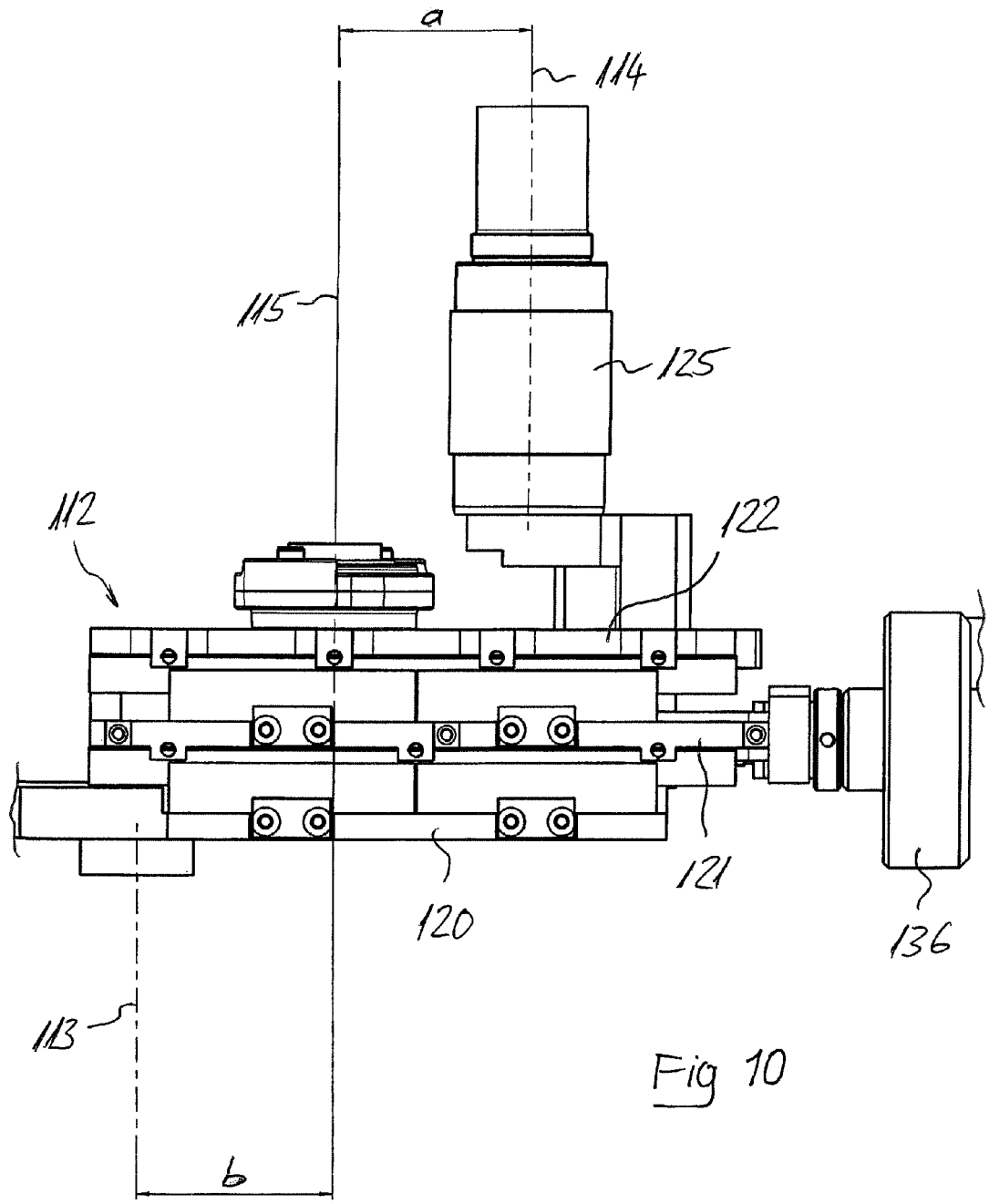
FIG. 10 is a view similar to FIG. 9, showing the C-slide displacement assembly in a second balanced condition which is different from the first balanced condition and in which there is a greater distance between the pivot support axis and the cross-lever axis.

The microscope stand illustrated in FIGS. 1 through 11 is a stand 11 for a surgical microscope, the stand including a C-shaped pivot support 12, a mount 22 attached to a first end 15 of pivot support 12 and adapted to mount microscope 16 to microscope stand 11, and further including a C-slide displacement assembly 112 provided on second end 13 of pivot support 12 for balancing the microscope about a pivot axis 114 associated with a stand interface 14.

The design of pivot support 12 is analogous to that of the pivot support according to one of the claims and figures of the applicant's international patent application WO 98/52484 A1 corresponding to U.S. Pat. No. 6,199,812. Pivot support 12 is pivotable about a support axis 113 defined by an axle held by C-slide displacement assembly 112.

C-slide displacement assembly 112 is pivotable about a pivot axis 114 relative to stand interface 14. All pivoting movements can be suppressed by braking force, the figures (e.g., FIG. 3) showing only brake 125 at pivot axis 114 by way of example.

Mount 22 is connected to pivot support 12 via a braking device 25 fixedly mounted with respect to the pivot support and is pivotable about mount axis 111. Mount 22 is supported for rotation about a first axis of rotation 23 so that it is rotatable relative to pivot support 12 and capable of being braked, the mount being connected to a brake via braking force transmission means disposed in a housing of braking device 25. Mount 22 includes a connection plate having holes 24 through which fastening elements can be passed for attachment of microscope 16 thereto. Mount 22, and the braking force transmission means for this mount 22, are designed according to one of the claims and figures of German patent application no. 10 2010 010 133.8 filed on the same day (Mar. 4, 2010) as German patent application no. 10 2010 010 131.1 from which the present application claims priority.

Stand interface 14 serves for attachment to at least one further support arm of the microscope stand, for example, to a ceiling mount, a floor stand, or to a wall mount. In this example, stand interface 14 is mounted to a ceiling bracket (not shown here), which allows attachment of microscope stand 11 to a ceiling. Stand interface 14 is rotatable about a rotation axis 124 relative to the ceiling bracket. This rotation axis 124 intersects pivot axis 114, and pivot support 12 carrying the microscope can be balanced relative to these two axes 124 and 114 by means of C-slide displacement assembly 112.

Pivot support 12 is held to stand interface 14 by a parallel guide mechanism 116, which allows pivot support 12 to perform a circular motion in a vertical plane. According to the present invention, parallel guide mechanism 116 is formed by a cross-lever linkage which is rotatable about a cross-lever axis 115 extending centrally between and parallel to support axis 113 of pivot support 12 and pivot axis 114 of C-slide displacement assembly 112. The cross-lever linkage is connected to both stand interface 14 and pivot support 12 in such a way that it transmits its own pivotal state simultaneously and equally to stand interface 14 and to pivot support 12.

The cross-lever linkage includes a cross lever 117, which is rotatably supported about cross-lever axis 115. Cross lever 117 is articulated at one end to stand interface 14 via a first connecting element 118 and at its other end to pivot support 12 via a second connecting element 119.

First connecting element 118 is articulated to the corresponding end of cross lever 117 via a first pivot point 126 and to stand interface 14 via a second pivot point 127. First connecting element 118 is curved between pivot points 126 and 127. Similarly, second connecting element 119 is articulated to the corresponding other end of cross lever 117 via a first pivot point 131 and to pivot support 12 via a second pivot point 132. Second connecting element 119 is curved between pivot points 131 and 132 as well. Connecting elements 118 and 119 are arranged with respect to each other such that their curvatures point away from each other. In this exemplary embodiment, cross lever 117 lies in a plane defined by connecting elements 118 and 119 and extending between stand interface 14 and C-slide displacement assembly 112.

Figure 14:
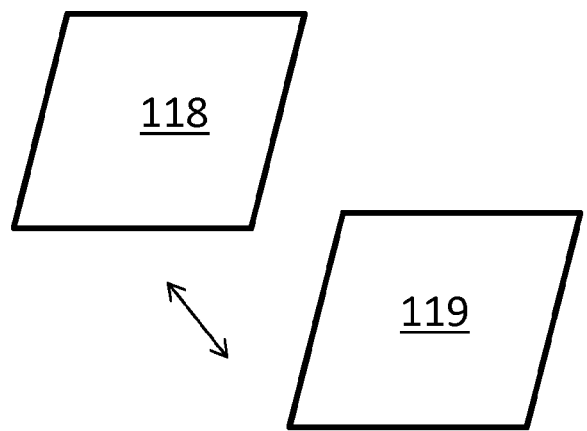
FIG. 14 is a is a block diagram schematically showing another embodiment of the first and second connecting elements.

In a variant shown in FIG. 14, the connecting elements 118, 119 of the cross-lever linkage lie in two different planes which are parallel to each other. In that variant, the cross lever of such a cross-lever linkage is advantageously disposed between the connecting elements in a plane extending between the respective planes of the connecting elements.

Figure 13:
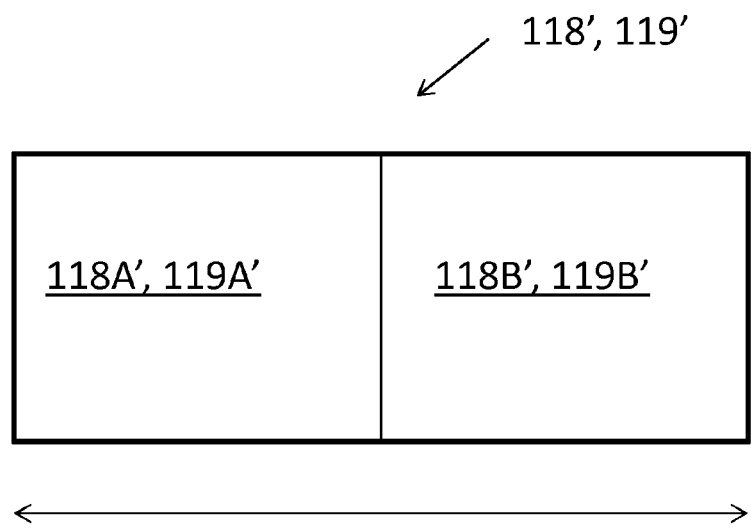
FIG. 13 is a block diagram schematically showing an embodiment of the first and second connecting elements.

In another variant shown in FIG. 13, at least one of the connecting elements 118', 119' is adjustable in length, for example, to permit specific lever ratios of the cross-lever linkage. The corresponding connecting element may, for example, be formed in two parts 118A', 118B', 119A', 119B', the two parts of the connecting element being fixable relative to one another in overlapping relationship according to the length to be obtained. In such a variant of the cross-lever linkage, advantageously, both connecting elements 118', 119' are adjustable in length.

Cross-lever axis/axle 115 is floatingly supported between support axis 113 of pivot support 12 and pivot axis 114 of C-slide displacement assembly 112. Cross-lever axis/axle 115 is supported in C-slide displacement assembly 112 in such a way that, during adjustment of the C-slide, its relative spatial position remains unchanged, while support axis 113 of pivot support 12 and pivot axis 114 of C-slide displacement assembly 112 come closer together or move further apart.

C-slide displacement assembly 112 includes a double parallel slide assembly including three slide plates 120, 121 and 122 disposed in three planes. The two outer slide plates 120 and 122 hold central slide plate 121 floatingly in a sandwich-like manner. Central slide plate 121 holds cross-lever axis/axle 115, which has a radial clearance relative to outer slide plates 120 and 122. Outer slide plate 120, which faces pivot support 12, supports support axis/axle 113 of pivot support 12, while outer slide plate 122, which faces stand interface 14, supports pivot axis/axle 114 of C-slide displacement assembly 112.

Outer slide plates 120 and 122 can be manually moved mirror-symmetrically relative to central slide plate 121 by means of a spindle 123. This ensures that after each adjustment of C-slide displacement assembly 112 by means of spindle 123, the distance a of cross-lever axis/axle 115 from support axis/axle 113 held by outer slide plate 120 is equal to the distance b of cross-lever axis/axle 115 from pivot axis/axle 114 held by outer slide plate 122. This feature is illustrated schematically in FIG. 7. Also advantageously, cross lever 117 is centrally pivoted about its cross-lever axis 115, so that in each of its positions, the distance c of cross-lever axis 115 from first pivot point 126 of first connecting element 118 is equal to the distance d of cross-lever axis 115 from first pivot point 131 of second connecting element 119 (see FIG. 7).

In an alternative variant not shown herein, one of the outer slide plates is moved by the spindle through a certain distance relative to the central slide plate, and the central slide plate is simultaneously moved through the same distance relative to the other outer slide plate. In this embodiment, too, it is ensured that after each adjustment of the C-slide displacement assembly by means of the spindle, the distance of the support axis from the cross-lever axis is equal to the distance of the pivot axis from the cross-lever axis.

Since, in the region of the stand interface, the stand can be regarded as having an absolutely fixed position in space, this design has the effect that during a balancing operation, central slide plate 121 is displaced by a certain distance relative to outer slide plate 122, while outer slide plate 120 is displaced by twice that distance in the same direction.

For ease of operation of spindle 123, the spindle is provided with an easy-to-grip handwheel 136. However, the spindle may also be driven by electric motor means. Spindle 123 is supported on central slide plate 121. As is shown particularly in FIG. 8, spindle 123 has a first threaded sleeve 137 and a second threaded sleeve 138 provided thereon, each of which mates with a corresponding outer slide plate 120 or 122. Threaded sleeves 137 and 138 are identical in design and are disposed on spindle 123 in such a way that their threads are oppositely directed. As an alternative to manual operation, the spindle may also be equipped with and driven by a motor, e.g., an electric motor.

Figure 11:
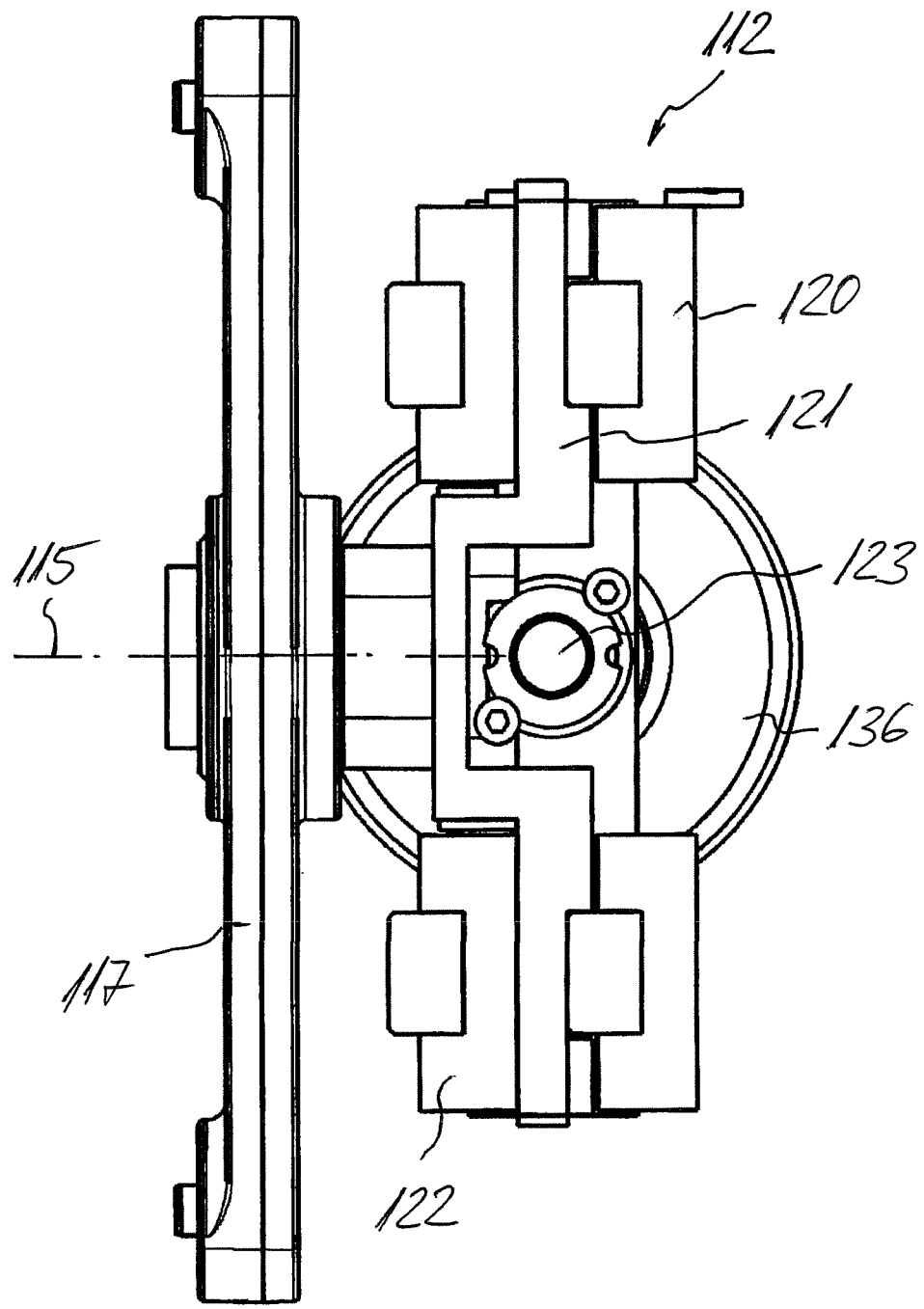
FIG. 11 is a view analogous to that of FIG. 6, but inverted, showing a detail of the C-slide displacement assembly.
Figure 12:
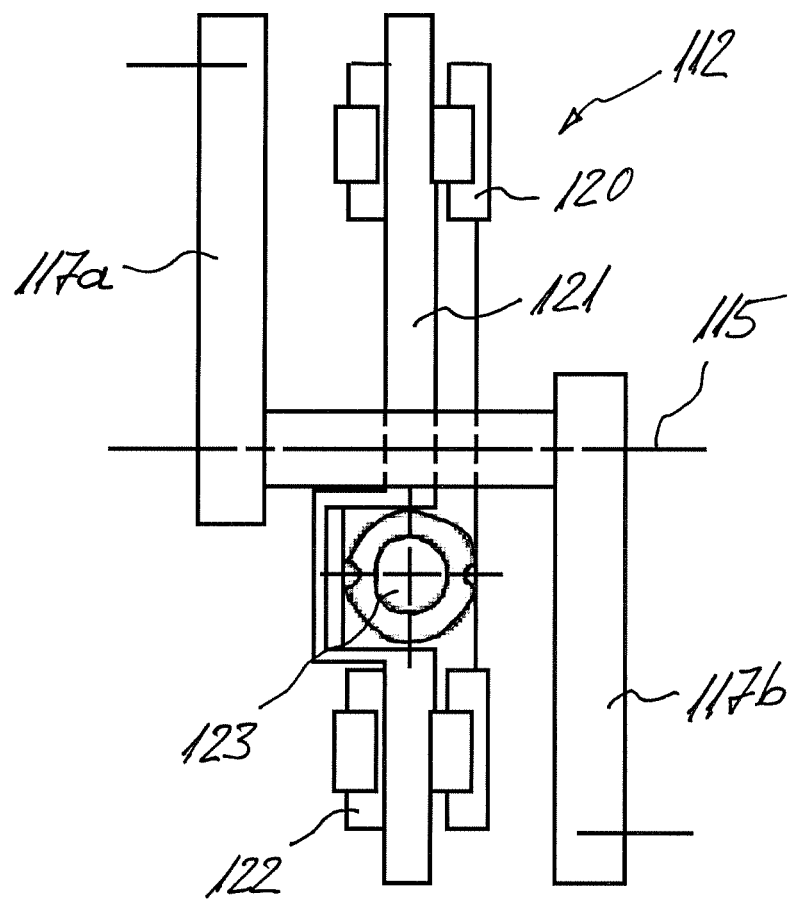
FIG. 12 is a detail view similar to FIG. 11, but showing a cross lever which is divided into two parts.

The design illustrated in FIG. 12 differs from that of FIG. 11 in that the cross lever is divided into two cross-lever arms 117a and 117b, which lie in respective planes lateral to C-slide displacement assembly 112 and are interconnected by cross-lever axis/axle 115.

SUMMARY OF PREFERRED EMBODIMENTS

Preferably, the cross-lever linkage includes a cross lever which is supported in the C-slide displacement assembly so that it is rotatable about the cross-lever axis/axle and which is articulated at one end to the stand interface via a first connecting element and at its other end to the pivot support via a second connecting element. The cross lever and the connecting elements constituting the lever linkage ensure vertical orientation of the microscope during pivoting of the pivot support. In addition, this embodiment of the cross-lever linkage enables a particularly compact design of this portion of the microscope stand.

Preferably, the cross-lever axis/axle is floatingly supported between the pivot support axis and the pivot axis of the C-slide displacement assembly, so that the axes can easily be displaced relative to each other. In this context, the term "floatingly supported" is understood to mean that the cross-lever axis/axle is supported in such a way that it is neither connected in a fixed relationship to the pivot support, nor to the stand interface. During displacement of the displaceable axes, these axes are, as it were, displaced relative to the cross-lever axis. Thus, the cross-lever axis is in a position which is spatially relatively fixed, but floating with respect to the two displaceable axes. In this context, the term "spatial" is understood to refer to the relative position in space.

Preferably, at least one connecting element is curved between its pivot points, which allows for optimal space utilization, enabling a particularly compact design of this portion of the microscope stand. Advantageously, both connecting elements are curved between their respective pivot points. Particularly advantageously, the connecting elements are arranged with respect to each other such that their curvatures point away from each other.

In one variant, at least one of the connecting elements is adjustable in length, which allows the lever ratios of the cross-lever linkage to be adjusted as needed.

Preferably, the cross lever lies in a plane defined by the connecting elements and extending between the stand interface and the C-slide displacement assembly. In this context, a cross lever that is slightly offset with respect to the connecting elements, for example because of the configuration of the mounting elements that connect the cross lever to the connecting elements, will still be regarded as lying in the plane defined by the connecting elements. Because of this feature, an even more compact design can be achieved for this portion of the microscope stand, and the tilting forces occurring in the pivot points of the cross-lever linkage are kept small If these tilting forces are of less importance, the cross lever may also be divided, so that one half of the lever is disposed on one side of the C-slide displacement assembly and the other half is disposed on the other side of the C-slide displacement assembly. In this case, the cross-lever axis/axle connects the two lever halves or arms.

Preferably, the cross-lever axis/axle, respectively the cross lever, is supported in the C-slide displacement assembly in such a way that, during adjustment of the C-slide, its relative spatial position remains unchanged, while the pivot support axis and the pivot axis of the C-slide displacement assembly come closer together or move further apart. Thus, during displacement of the C-slide, the axis/axle of the support and the pivot axis/axle are displaced relative to the cross-lever axis/axle, which allows a simple design for the C-slide displacement assembly. In this context, too, the term "spatial" is understood to refer to the relative position in space.

Preferably, the C-slide displacement assembly includes a double parallel slide assembly including three slide plates disposed in three parallel planes, the two outer slide plates floatingly holding the central slide plate in a sandwich-like manner, and the central slide plate holding the cross-lever axis/axle, which has a radial clearance relative to the outer slide plates, the central slide plate further preferably holding an adjustment mechanism. This embodiment of the C-slide displacement assembly allows it to be built in a compact way, making this portion of the microscope stand compact and easy to manufacture. Moreover, in comparison with the known C-slide displacement designs, such as are known, for example, from the cited prior art, the average overall length of the C-slide is shorter, but the maximum balancing path is relatively equal in length.

Preferably, the outer slide plate facing the pivot support supports the pivot support axis/axle, while the outer slide plate facing the stand interface supports the pivot axis/axle of the C-slide displacement assembly. These measures enable easy manufacture and a sturdy design, while providing a compact C-slide displacement assembly. In this context, the term "support" is understood to include also "non-rotatably receive".

Preferably, at least one of the outer slide plates can be moved manually or by motor means relative to the central slide plate by means of a spindle. The spindle has a thread which mates in each case with one complementarily shaped part (threaded sleeve) provided on the particular, corresponding outer slide plate. The desired travel paths of the slide plates relative to each other can be easily defined by configuring the threads accordingly. Advantageously, the two outer slide plates are movable by the spindle relative to each other and relative to the central slide plate. Particularly advantageously, the central slide plate and one of the outer slide plates can be moved by the same spindle relative to the other outer slide plate, and the two threaded sleeves and the thread of the spindle have the same pitch, so that when the spindle is operated, the threaded sleeves are simultaneously moved through the same distance.

Preferably, the outer slide plates are movable by the spindle mirror-symmetrically relative to the central slide plate, so that the C-slide displacement assembly, and thus the C-slide, can be made particularly compact and, therefore, require little space. The two outer slide plates are moved relative to each other in such a way that the axes/axles supported thereon (the axis/axle of the support and the pivot axis/axle) are equally spaced from the cross-lever axis/axle. This ensures a balanced configuration of the cross-lever linkage elements following each adjustment of the C-slide displacement assembly. This means that the movement of the two outer slide plates relative to each other is compensated by the movement of the central slide plate through half the travel path length so as to maintain the cross-lever axis/axle centrally with respect to the axis/axle of the support and the pivot axis/axle.

Thus, one of the outer slide plates is movable by the spindle through a certain distance relative to the central slide plate, and the central slide plate is movable through the same distance relative to the other outer slide plate. This design of the C-slide displacement assembly is much more compact and, therefore, is also advantageous.

A technical reversal of this configuration is also within the scope of this application.

In an alternative embodiment according to the present invention, the connecting elements do not lie in a common plane, but in two different planes which are parallel to each other. This allows for an increased pivoting range of the pivot support. To accommodate tilt loads which may occur in the pivot points of the cross-lever linkage, the pivot points are advantageously of sufficiently massive construction.

Preferably, the mount and the braking force transmission means for this mount are designed according to one of the claims of commonly owned German patent application number 10 2010 010 133.8 filed Mar. 4, 2010, which makes it possible to make a microscope stand, in particular a stand for a surgical microscope, that, in addition to the aforementioned advantages, also has the advantages of said mount and of said braking force transmission means. The aforementioned German patent application number 10 2010 010 133.8 is incorporated herein by reference in its entirety in order to allow a later combination of the two applications based on the same priority.

Preferably, the pivot support is designed according to one of the claims of international patent application WO 98/52484 A1, which makes it possible to make a microscope stand, in particular a stand for a surgical microscope, that, in addition to the aforementioned advantages, also has the advantages of said pivot support. U.S. Pat. No. 6,199,812 corresponding to international patent application WO 98/52484 A1 is incorporated herein by reference in its entirety in order to allow a later combination of the two or three applications based on the same priority. For a description of the pivot support, reference is explicitly made to the figures and their description in the cited U.S. Pat. No. 6,199,812 and corresponding international application WO 98/52484 A1.

LIST OF REFERENCE NUMERALS 11 microscope stand
12 pivot support
13 second end of 12
14 stand interface
15 first end of 12
16 microscope
22 mount
23 $1^{st}$ axis of rotation
24 hole in 22
25 braking device
111 lower support axis (mount axis)
112 C-slide displacement assembly
113 support axis
114 pivot axis
115 cross-lever axis
116 parallel guide mechanism
117 cross lever
118, 118' $1^{st}$ connecting element to 14
118A', 118B' a $1^{st}$ connecting element part
118B', 119B' a $2^{nd}$ connecting element part
119, 119' $2^{nd}$ connecting element to 12
120 outer slide plate facing 12
121 central slide plate
122 outer slide plate facing 14
123 spindle
124 rotation axis of 14
125 brake
126 $1^{st}$ pivot point of 118
127 $2^{nd}$ pivot point of 118
131 $1^{st}$ pivot point of 119
132 $2^{nd}$ pivot point of 119
136 handwheel
137 $1^{st}$ threaded sleeve
138 $2^{nd}$ threaded sleeve

What is claimed is:

1. A microscope stand for supporting a surgical microscope, the stand comprising:
a stand interface;
a pivot axis associated with the stand interface;
a pivot support including a first end and a second end;
a mount attached to the first end of the pivot support and adapted to mount the microscope to the microscope stand;
a C-slide displacement assembly provided on the second end of the pivot support for balancing the microscope about the pivot axis; and
a support axis held by the C-slide displacement assembly;
the pivot support being pivotable about the support axis;
the C-slide displacement assembly being pivotable about the pivot axis relative to the stand interface; and
a parallel guide mechanism connecting the pivot support to the stand interface and allowing the pivot support to perform a circular motion in a vertical plane, wherein the parallel guide mechanism includes a cross-lever linkage which is rotatable about a cross-lever axis extending centrally between and parallel to the support axis and the pivot axis and which is connected to both the stand interface and the pivot support in such a way that the cross-lever linkage transmits its own pivotal state simultaneously and equally to the stand interface and to the pivot support, and wherein the cross-lever linkage includes a cross lever supported for rotation about the cross-lever axis, the cross lever being articulated at one end thereof to the stand interface via a first connecting element and at another end thereof to the pivot support via a second connecting element.

2. The microscope stand as recited in claim 1, wherein the cross-lever axis is floatingly supported between the support axis of the pivot support and the pivot axis of the C-slide displacement assembly.

3. The microscope stand as recited in claim 1, wherein the first connecting element has two pivot points and the second connecting element has two pivot points, wherein at least one of the first and second connecting elements is curved between its two pivot points.

4. The microscope stand as recited in claim 1, wherein at least one of the first and second connecting elements is adjustable in length.

5. The microscope stand as recited in claim 1, wherein the cross lever lies in a plane defined by the first and second connecting elements and extending between the stand interface and the C-slide displacement assembly.

6. The microscope stand as recited in claim 1, wherein the cross lever is divided into two cross-lever arms and each of the two cross-lever arms lies in a different respective plane lateral to the C-slide displacement assembly, one of the respective planes extending between the stand interface and the C-slide displacement assembly and the other of the respective planes extending between the pivot support and the C-slide displacement assembly, and the two cross-lever arms being rigidly interconnected along cross-lever axis.

7. The microscope stand as recited in claim 1, wherein the cross-lever axis is supported in the C-slide displacement assembly in such a way that, during adjustment of the C-slide displacement assembly, a relative spatial position of the cross-lever axis remains unchanged, while the support axis of the pivot support and the pivot axis of the C-slide displacement assembly come closer together or move further apart.

8. The microscope stand as recited in claim 1, wherein the C-slide displacement assembly includes a double parallel slide assembly having three slide plates disposed in three planes, the three slide plates comprising two outer slide plates and a central slide plate floatingly held by the two outer slide plates in a sandwich-like manner, and the central slide plate holds a cross-lever axle defining the cross-lever axis wherein the cross-lever axle has a radial clearance relative to the outer slide plates.

9. The microscope stand as recited in claim 8, wherein one slide plate of the two outer slide plates faces the pivot support and supports the support axis of the pivot support, while another slide plate of the two outer slide plates faces the stand interface and supports the pivot axis of the C-slide displacement assembly.

10. The microscope stand as recited in claim 8, wherein at least one of the two outer slide plates is movable relative to the central slide plate by means of a spindle.

11. The microscope stand as recited in claim 10, wherein the two outer slide plates are movable by the spindle mirror-symmetrically relative to the central slide plate.

12. The microscope stand as recited in claim 10, wherein one of the two outer slide plates is movable by the spindle through a certain distance relative to the central slide plate, and the central slide plate is movable through the same certain distance relative to the other of the two outer slide plates.

13. The microscope stand as recited in claim 1, wherein the first and second connecting elements lie in a common plane.

14. The microscope stand as recited in claim 1, wherein the first and second connecting elements lie in two different planes which are parallel to each other.

* * * * *